US010478086B2

(12) United States Patent
Schalk et al.

(10) Patent No.: US 10,478,086 B2
(45) Date of Patent: Nov. 19, 2019

(54) MEASUREMENT OF CORTICAL EXCITABILITY

(71) Applicant: HEALTH RESEARCH, INC., Menands, NY (US)

(72) Inventors: Gerwin Schalk, Glenmont, NY (US); Peter Brunner, Delmar, NY (US); William G. Coon, Cranston, RI (US); Adriana De Pesters, Coppet (CH)

(73) Assignee: HEALTH RESEARCH, INC., Menands, NY (US)

( * ) Notice: Subject to any disclaimer, the term of this patent is extended or adjusted under 35 U.S.C. 154(b) by 116 days.

(21) Appl. No.: 15/558,780

(22) PCT Filed: Mar. 17, 2016

(86) PCT No.: PCT/US2016/022946
§ 371 (c)(1),
(2) Date: Sep. 15, 2017

(87) PCT Pub. No.: WO2016/149538
PCT Pub. Date: Sep. 22, 2016

(65) Prior Publication Data
US 2018/0070847 A1    Mar. 15, 2018

Related U.S. Application Data

(60) Provisional application No. 62/134,488, filed on Mar. 17, 2015.

(51) Int. Cl.
*A61B 5/0484*    (2006.01)
*A61N 1/36*    (2006.01)
(Continued)

(52) U.S. Cl.
CPC ........ *A61B 5/0484* (2013.01); *A61B 5/04001* (2013.01); *A61B 5/04017* (2013.01);
(Continued)

(58) Field of Classification Search
CPC ........................................ A61B 5/0476–04845
(Continued)

(56) References Cited

U.S. PATENT DOCUMENTS 7,551,956 B2    6/2009    Osorio et al.
2007/0100278 A1    5/2007    Frei et al.
(Continued)

OTHER PUBLICATIONS

Patent Cooperation Treaty, International Search Report for PCT/US2016/022946 dated Jun. 3, 2016, 2 pages.
(Continued)

*Primary Examiner* — Amanda K Hulbert
*Assistant Examiner* — Philip C Edwards
(74) *Attorney, Agent, or Firm* — Heslin Rothenberg Farley & Mesiti P.C.

(57) ABSTRACT

The present invention includes a responsive neural stimulator having electrodes, a filter, a processor, a recording medium, an extractor for extracting instantaneous voltage amplitudes of biased oscillatory activity with asymmetrically distributed peak/trough amplitudes, and a neural stimulator connected to the processor configured to apply neural stimulation via the neural stimulator when a predetermined state of neuronal excitability is detected, a state of relatively higher neuronal excitability corresponding to a relatively lower instantaneous voltage amplitude extracted by the extractor. Also provided is a system for providing neurofeedback including electrodes, a filter, a processor, a recording medium, an extractor for extracting instantaneous voltage amplitudes of biased oscillatory activity with asymmetrically distributed peak/trough amplitudes, and an output device configured to communicate changes in, increases in, decreases in, or maintenance of instantaneous voltage amplitudes, or any combination, to a participant in a neurofeedback session.

20 Claims, 8 Drawing Sheets

(51) Int. Cl.
  *A61B 5/04*   (2006.01)
  *A61B 5/0478*  (2006.01)
  *A61B 5/00*   (2006.01)

(52) U.S. Cl.
  CPC .......... *A61B 5/0478* (2013.01); *A61B 5/4836* (2013.01); *A61N 1/36064* (2013.01); *A61N 1/36067* (2013.01); *A61N 1/36071* (2013.01); *A61N 1/36139* (2013.01)

(58) Field of Classification Search
  USPC ........................................................ 607/45
  See application file for complete search history.

(56) References Cited

U.S. PATENT DOCUMENTS

| | | | |
|---|---|---|---|
| 2009/0264789 A1* | 10/2009 | Molnar | A61N 1/36135 600/544 |
| 2011/0137371 A1 | 6/2011 | Giftakis et al. | |
| 2013/0303933 A1 | 11/2013 | Bonnstetter et al. | |
| 2015/0066104 A1 | 3/2015 | Wingeier et al. | |

OTHER PUBLICATIONS

Patent Cooperation Treaty, Written Opinion of the International Searching Authority for PCT/US2016/022946 dated Jun. 3, 2016, 4 pages.

Schalk, "A general framework for dynamic cortical function: the function-through-biased-oscillations (FBO) hypothesis," Jun. 2015, pp. 1-10, Hypothesis and Theory, Frontiers in Human Neuroscience, vol. 9, Article 352.

\* cited by examiner

MEASUREMENT OF CORTICAL EXCITABILITY

GOVERNMENT RIGHTS STATEMENT

This invention was made with government support under EB000856 awarded by the NIH, EB018783 awarded by the NIH and W911NF1410440 awarded by the ARMY/ARO. The government has certain rights in the invention.

CROSS-REFERENCE TO RELATED APPLICATIONS

This application is a national stage filing under section 371 of International Application No. PCT/US20106/022946, filed on Mar. 16, 2016, published in English on Sep. 22, 2016, which claims priority under 35 U.S.C. § 119 to U.S. Provisional Application No. 62/134,488, filed Mar. 17, 2015, which are herein incorporated by reference in their entireties.

FIELD OF THE INVENTION

The present invention relates to, inter alia, systems, methods, and devices for the improved measurement of cortical excitability.

BACKGROUND OF THE INVENTION

Many scientific or applied investigations of brain function depend on an assessment of the degree of activation of a particular brain area. More formally, this degree of activation can be expressed by measurements of cortical excitation or cortical excitability. Cortical excitation describes the degree of activation of a particular area of the brain. Cortical excitability describes the likelihood that a particular area of the brain gets excited. Thus, the two measurements are closely related: on average, the higher cortical excitability in a certain area of the brain, the higher its excitation.

Accurate measurements of cortical excitability are very important. First, certain brain signal measurement modalities cannot directly measure cortical excitation. For example, scalp-recorded EEG cannot readily access brain activity at those high frequencies (typically >40 Hz) that index cortical excitation. Second, in certain application domains, it may be important to measure cortical excitability instead of cortical excitation. For example, the human faculty of attention (e.g., when one expects to hear a tone compared to seeing something) is realized by the brain by regulating the degree of cortical excitability, e.g., increasing cortical excitability in auditory brain areas, and decreasing excitability in visual brain areas.

It has long been known that a principal mechanism of the brain to regulate cortical excitability is to change specific properties of oscillations across different areas of the brain. In particular, many previous studies have linked the power or the phase of cortical oscillations to cortical excitability. However, there still exists the need for more accurate ways of measuring and predicting cortical excitation.

The present invention is directed to overcoming these and other deficiencies in the art.

SUMMARY OF THE INVENTION

The present invention relates to, inter alia, a responsive neural stimulator including a recording electrode or electrodes connected to a filter, a processor connected to the filter wherein the processor which includes a recording medium for recording brain waves detected by the electrode or electrodes and an extractor for extracting instantaneous voltage amplitudes of biased oscillatory activity, with biased oscillatory activity including asymmetrically distributed peak/trough amplitudes, and a neural stimulator connected to the processor, the processor, the neural stimulator, or both configured to apply neural stimulation via the neural stimulator when a predetermined state of neuronal excitability is detected, such that a state of relatively higher neuronal excitability comprises a relatively lower instantaneous voltage amplitude extracted by the extractor.

The present invention also relates to a system for providing neurofeedback including a recording electrode or electrodes connected to a filter, a processor connected to the filter where the processor includes a recording medium for recording brain waves detected by the electrode or electrodes and an extractor for extracting instantaneous voltage amplitudes of biased oscillatory activity, and biased oscillatory activity includes asymmetrically distributed peak/trough amplitudes, and an output device connected to the processor and configured to communicate changes in, increases in, decreases in, or maintenance of instantaneous voltage amplitudes, or any combination of two or more of the foregoing, to a participant in a neurofeedback session.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements. The foregoing and other objects, features, and advantages of the invention are apparent from the following detailed description taken in conjunction with the accompanying drawings in which.

DETAILED DESCRIPTION OF THE INVENTION

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

The present invention relates to, inter alia, systems, methods, and devices for the improved measurement of the excitability of neurons, including neurons in the central nervous system. In one aspect of the invention, improved measurement of the excitability neurons in the brain is provided, but the invention applies equally well to measuring excitability of other neurons, such as spinal neurons. Another aspect of the present invention relates to various applications for the use of the improved measurement of neural excitability, such as cortical excitability, although measurement of excitability of other brain or spinal neurons could also be similarly applied in accordance with the invention. Where cortical excitability is referenced herein, not only excitability of cortical neurons is contemplated, but also excitability of other neurons, elsewhere in the brain or central nervous system, may be substituted for cortical excitability in accordance with an aspect of the present invention. These and other aspects of the invention are further described in the present disclosure.

Figure 1:
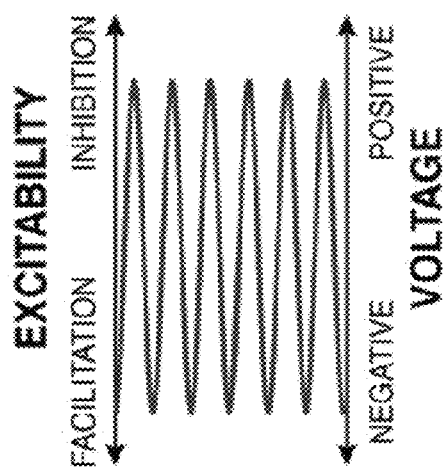
FIG. 1: Oscillatory voltage amplitude, the principal measurement that controls cortical excitability.

Conventional applications of using measurements of brain waves or other indicia of neural activity collected by population-level sampling techniques (including electroencephalogram (EEG), electrocorticography (ECoG), or local field potential recordings (LFP)) to determine states of neural excitability focus on using oscillatory power or phase of wave traces to draw conclusions about excitability. However, these measures lack a degree of accuracy desirable for rapid, fine-tuned, sensitive application of conclusions as to excitability based on population-level sampling. Oscillatory activity can dynamically modulate the excitability of local neuronal populations. For example, cortical neurons preferentially fire during the trough of neuronal oscillations in different frequency bands, such as the theta (4-8 Hz) or alpha (8-12 Hz) bands. According to the present invention, the instantaneous voltage amplitude of oscillations, rather than oscillatory power or phase, is the principal measurement that directly reflects cortical excitability. This relationship between cortical excitability and oscillatory voltage is represented in the exemplary oscillation illustrated in FIG. 1, where high facilitation of excitability corresponds to negative oscillatory voltages.

Figure 2A:
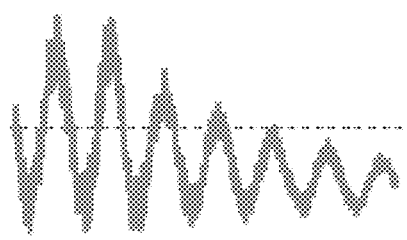
FIG. 2A: A noise voltage trace from an electroencephalogram (EEG).
Figure 2B:
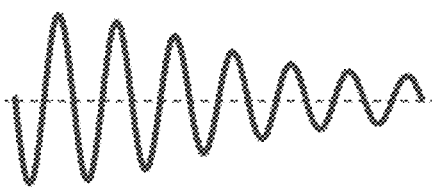
FIG. 2B: The voltage trace of FIG. 2A after it has been band-pass filtered.
Figure 2C:
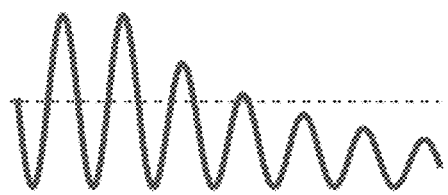
FIG. 2C: The band-pass filtered voltage trace of FIG. 2B back into which an estimate of the amplitude bias at each point in time has been added.

The voltage measurements detected using population-level sampling techniques, such as EEG, ECoG, LFP, or deep-brain electrodes, are affected not only by oscillatory activity, but also by asynchronous neuronal activity, voltage fluctuations caused by ionic flows, etc. This is reflected in the "noisy" voltage trace of an EEG recording shown in FIG. 2A. According to the present invention, the instantaneous amplitude of oscillations has to be extracted properly so as to maximally separate it from activity from other sources. In one aspect of the invention, the troughs of an oscillation are always at the same low voltage level, irrespective of the (peak-to-peak) amplitude difference between peaks and troughs. In other words, oscillations have an amplitude bias that, at each point in time, equals half the estimated peak-to-peak amplitude at that time. Thus, one possible, non-limiting example of a way to extract the instantaneous amplitude of biased oscillations begins by band-pass filtering oscillations in an appropriate frequency band (e.g., the alpha (8-12 Hz) band). This initial step will make the signal zero-mean (i.e., it varies about zero irrespective of the peak-to-peak amplitude at any given point in time). An example is illustrated in FIG. 2B. In a further aspect of the present invention, at each point in time, an estimate of the amplitude bias is added back into the band-pass filtered signal. The resulting signal represents the instantaneous voltage of the biased oscillation. An example is illustrated in FIG. 2C.

Figure 3A:
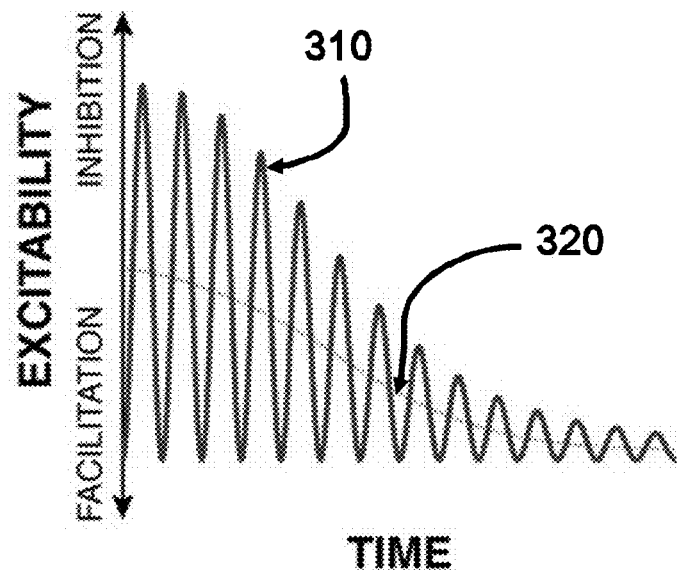
FIG. 3A: An oscillatory voltage trace with the amplitude bias shown as a dotted line.
Figure 3B:
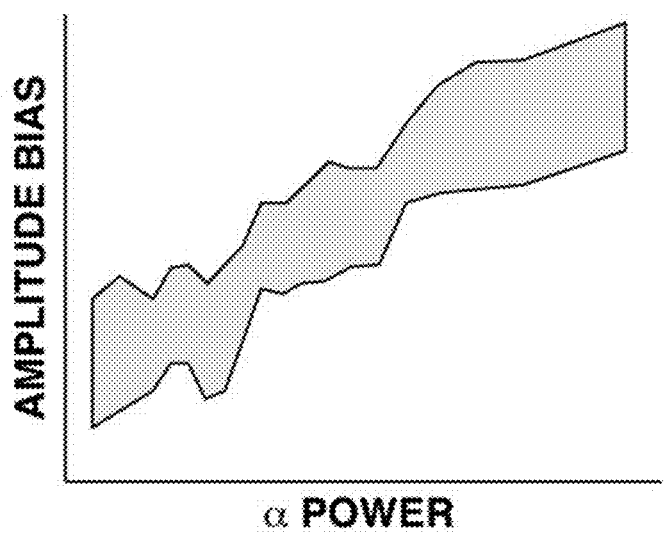
FIG. 3B: A graphical relationship of the relationship between the amplitude bias of an oscillation in the a band (y-axis) and the power of the oscillation (x-axis).

Oscillation's peak-to-peak amplitude (and hence, oscillatory power) is not constant but often changes with a task. The present invention applies the fact that such task-related changes in peak-to-peak amplitude do not affect the peaks and troughs of the oscillation equally. In the example illustrated in FIG. 3A, the voltage trace 310 gives the time course of oscillatory activity. The trace 310 has a bias 320, which could be computed by averaging one cycle of the oscillation or by averaging many trials with random oscillatory phase and whose amplitude varies with the amplitude of the oscillatory power of the trace. As illustrated in FIG. 3B, (modified from FIG. 3A, Nikulin et al., 2007, J. Neurosci., 25:3146-3154) the amplitude bias of an oscillation in the alpha band (y axis) is related to the power of the oscillation (x axis). The present invention applies the relationship between amplitude bias and oscillatory power to improve the measurement of cortical excitability.

In an aspect of the present invention, instantaneous voltage of biased oscillations may be extracted from voltage traces, in accordance with one nonlimiting example, as follows: (1) establish, for each value of oscillatory power, the bias; (2) apply a filter that recovers the oscillation (e.g., by applying a band-pass filter at the frequency of the oscillation); (3) measuring, at each point in time, the power of the resulting filtered oscillatory signal; and (4) for each point in time, reintroduce (i.e., add) the value of the bias that corresponds to that power of the oscillatory signal at that point in time.

Figure 4A:
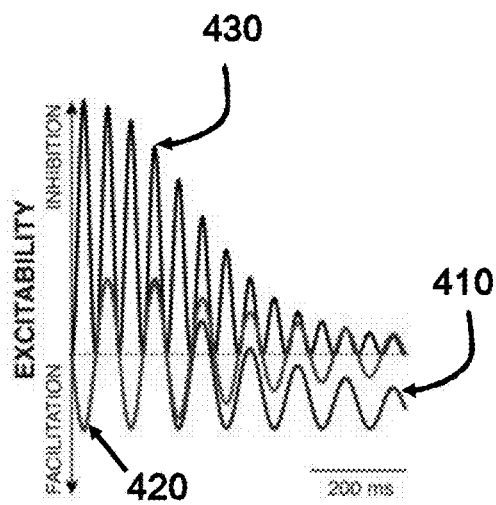
FIG. 4A: Different transformations of voltage traces.
Figure 4B:
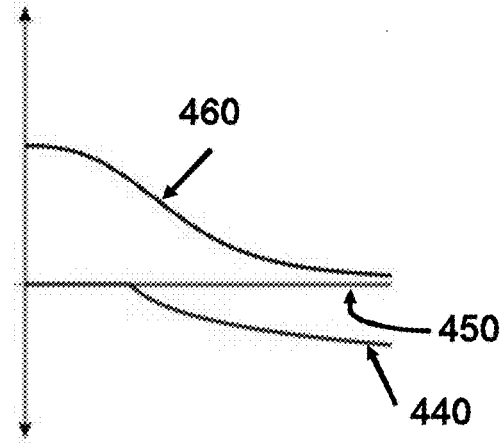
FIG. 4B: Traces of the averages of trials of corresponding signal traces shown in FIG. 4A.

The relationship between oscillatory bias and behavioral and neurological phenomena demonstrates the link between oscillatory bias and neural excitability. FIG. 4A shows a time-varying voltage amplitude of an exemplary 10-Hz biased oscillation 410. The result of a 10-Hz oscillation and a slow decrease in peak-to-peak amplitude, this trace reduces the voltage of its peak over about 1.5 sec., thereby indicating time-varying but still progressively increasing cortical excitability. There are several ways to extract oscillatory measurements from brain signals (including band-pass-filtering, Hilbert transform, and other known to skilled artisans), all of which could be adopted to and used in accordance with the present invention. The effect of band-pass filtering the exemplary biased oscillation between 8-12 Hz 420, now centered around zero, and the squared amplitude of the band-pass filtered trace 430, an illustration of the instantaneous power of the bandpass-filtered signal 420, are also shown. Shown in FIG. 4B are traces showing the average of many trials of the exemplary biased oscillation 440 (i.e., averaging trace 410 in FIG. 4A), the band-pass filtered oscillation 450 (i.e., averaging trace 420 in FIG. 4A), and the squared amplitude trace 460 (i.e., averaging trace 430 in FIG. 4A). The averaged voltage amplitude trace 440 highlights a trend toward increasing excitability (i.e., decreasing voltage amplitude).

Figure 4C:
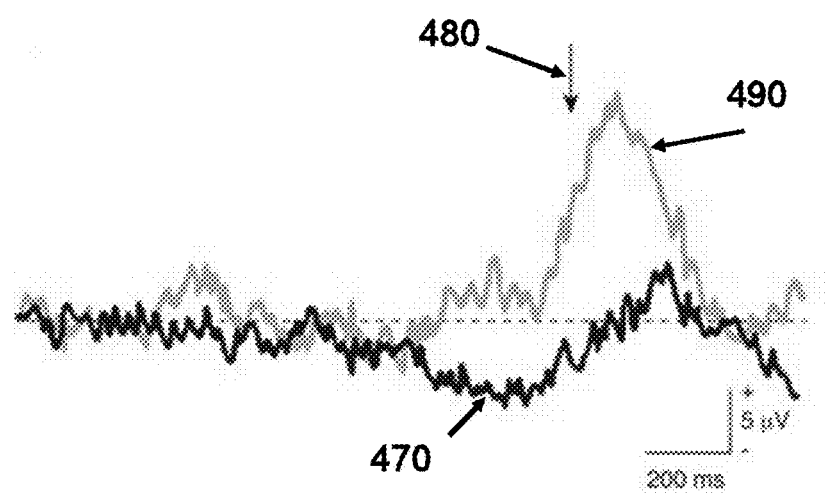
FIG. 4C: Voltage traces of EEG of the motor cortex in temporal relationship to movement.

In FIG. 4C (adapted from Shibasaki et al., 1978, J. Neurol. 219, 15-25) two traces are shown. The bottom trace shows the average voltage of EEG recordings 470 from sensorimotor cortex before initiation of movement 480 (signified by the black arrow). The negative deflection prior to movement onset in 470 is readily apparent and is similar to the averaged biased oscillation trace 410 in FIG. 4B. The upper trace 490 illustrates the average voltage of EEG recordings after a lesion to the nucleus ventralis intermedius of the thalamus, which projects to the motor cortex. This upper trace does not feature the negative deflection before movement but does exhibit an increased evoked response after movement. Thus, with the thalamocortical oscillator circuits intact, the negative deflection indicative of increased neuronal excitability is evidence, whereas after such circuit is lesioned no such negative voltage shift occurs presumably because the thalamic lesions often diminish alpha oscillations. Thus, in accordance with the present invention, amplitude bias in oscillatory activity is applied to correspond different slow-time-varying brain signal phenomena to particular brain states.

Figure 5A:
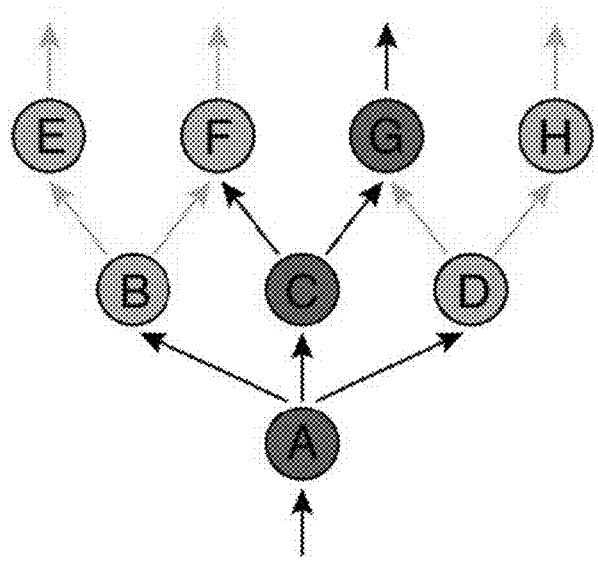
FIG. 5A: A model for regulation of information flow in the cortex by biased oscillations.

In another aspect of the present invention, population-level sampling techniques may be applied to identify dynamic task-related processing by the brain by using instantaneous voltage amplitude of biased oscillations such as predictive inhibition of task-unrelated populations or inhibition of populations at task-unrelated times. An exemplary network of neuronal populations is illustrated in FIG. 5A. Eight distinct neuronal populations are labeled with A-H. Anatomical connections between these populations are depicted with arrows. Arrows that do or do not carry action potential volleys are shown in black or gray, respectively. Populations that receive excitatory or inhibitory modulation (i.e., low or high average peak-to-peak voltage amplitude, respectively) are shown in dark gray or light gray, respectively. In this example, population A, which does not receive inhibitory modulation (e.g., from subcortical structures such as a particular thalamic nucleus), receives an action potential volley and sends out volleys to all populations it is connected to (B, C, and D), presumably through cortico-cortical projections. Because B and D receive inhibitory modulation, they are not excited by the incoming volleys they receive from A; thus, they do not send out volleys to connected populations. In this example, excitatory input to population A will result in activation of, and communication between, populations C and G. Because biased oscillatory voltage amplitude can define higher excitability either by decreasing peak-to-peak amplitude or by being in its trough, it can describe a situation in which a sending and a receiving neuronal population communicate either by synchronizing their phases or by decreasing the peak-to-peak amplitude of the receiving population.

Figure 5B:
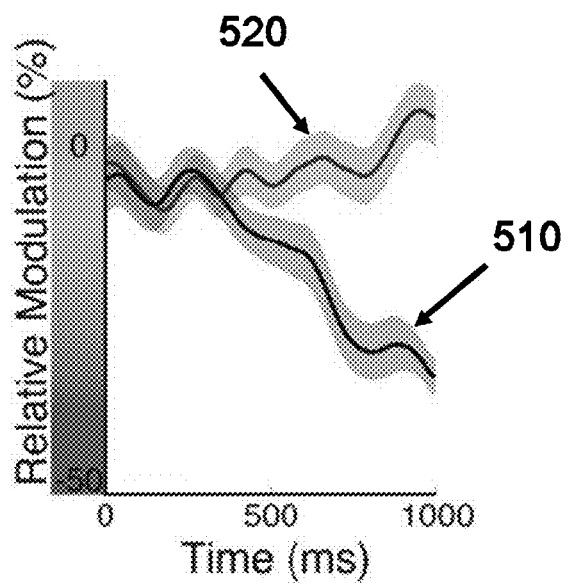
FIG. 5B: Time courses of sensorimotor cortex in a perceptual decision-making task.

FIG. 5B (modified from Kubanek et al., 2013, Neuroimage 83, 795-808) illustrates the relative power (i.e., a function of peak-to-peak amplitude) of an oscillatory signal recorded over sensorimotor cortex in a perceptual decision task, in which subjects were asked to push a button depending on the amount of evidence given by auditory clicks. The power of the modulatory signal is progressively reduced for trials of "high" evidence 510 compared to for trials of "low" perceptual evidence 520. Thus, this mechanism progressively increases cortical excitability in motor cortex, and clearly demonstrates that cortical excitability of local neuronal populations depends not only on present but also on past events.

The present invention applies these relationships between voltage-biased oscillations of brain waves and neural excitability to improve measurements of neuronal excitability and applies the improved measurements to various purposes. For example, electrical stimulation of the brain can be useful for various purposes. One exemplary purpose is to terminate epileptic seizures (Nune et al., 2015, Current Treatment Options in Neurology, 17:1-6). In order to minimize side effects of that stimulation, it is desirable to stimulate the brain at times at which seizures actually occur (i.e., to only deliver therapy when it is actually needed) (Morrell et al., Neurosurgery Clinics of North America, 2016 27:111-21.) Such therapy is termed "responsive" as it is responsive to the current state of the brain. The applicability of this responsive approach to electrical stimulation of the brain is currently evaluated not only in the context of epileptic seizures, but also in movement disorders (Parkinson's disease or Tourette syndrome) or other conditions. Other examples include responsive stimulation of neural centers controlling descending pain-inhibition pathways or other pain-modulatory pathways for the management or treatment of chronic pain (Bittar et al., 2005, J. Clin. Neurosci., 12:515-519), and for the treatment of mood disorders including obsessive-compulsive disorder and major depression (Velasques et al., 2014, CNS Neurol. Disord. Drug Targets, 13:961-971). For determining occurrence of a seizure, it is not always necessary for a physical seizure to occur; rather, patterns of neural activity redictive of or characteristic of a seizure may be detected and signal an opportune time for prevention, delay, or cessation of a seizure. Similarly, measurements of neural excitability may help determine when and, if more than one region is in contact with a neural stimulator and/or electrodes for measurement, where stimulation should be applied, for how long and how much, and other parameters, suitable to the applications listed above (e.g., treatment of movement, behavioral, or mood disorders).

While conventional approaches base a decision to deliver therapy on a particular diagnosis of a disease state (e.g., whether or not an epileptic seizure is present) and in many instances have identified particular cortical or other specific brain loci where neural stimulation has desirable effects depending on symptoms, conventionally, none of them consider the moment-to-moment receptivity of the brain (i.e., neural excitability) to determine the precise moment in which electrical stimulation best be delivered. In accordance with the present invention, the moment-to-moment variations of the instantaneous voltage of biased oscillations are used to determine the most receptive times to deliver electrical stimulation (e.g., stimulate only when the instantaneous voltage is low (i.e., cortical excitability is high)), or stimulate only when cortical excitability at other locations is low (to minimize the possibility that additional seizures are triggered), and time the application of neural stimulation to the intended region or regions. Skilled artisans with an ordinary understanding of the current, conventional state of technology of the application of responsive neural stimulation would be capable of adapting detecting, filtering, and extracting of instantaneous voltage of biased oscillations in responsive brain stimulation disclosed herein to known methods, apparatuses, and systems for responsive neural stimulation, in accordance with the present invention.

Figure 6:
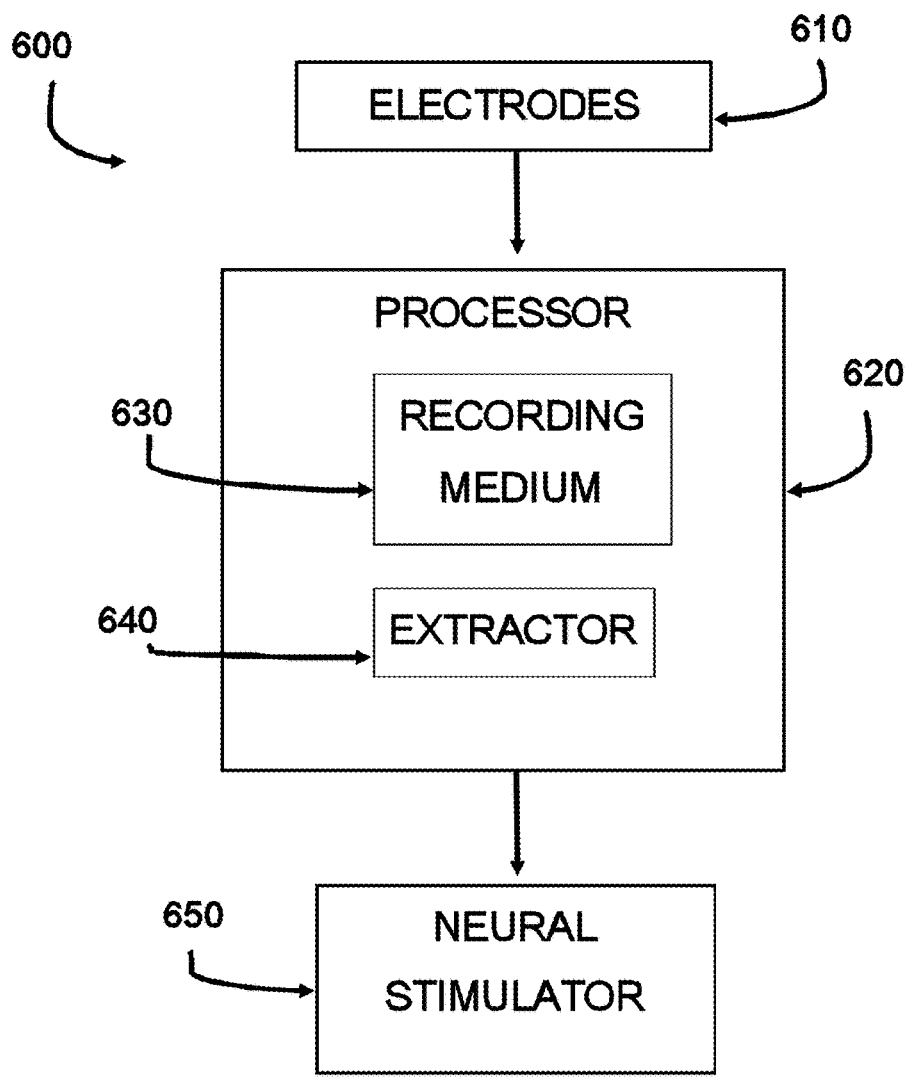
FIG. 6: A responsive neural stimulator in accordance with an embodiment of the present invention.

Referring to a non-limiting example shown in FIG. 6, shown is an embodiment of the present invention in the form of a responsive neural stimulator 600. Electrodes 610 are attached to a subject, such as a human subject, and can be placed where measurement of neural excitability is desired for a given application, such as on the surface of the scalp in the case of EEG, the surface of the cortex in the case of ECoG, below the surface of and within the brain such as for deep brain stimulation, on the surface of or within the spinal cord, etc. Rather than multiple electrodes 610, simply one recording electrode may be placed on or within a subject, such as if there is only one locus from which information as to excitability state is desired. In addition to recording electrodes 610, reference electrodes may also be applied, in accordance with conventional population-level sampling techniques, as would be appreciated by those with ordinary skill in this field. Electrodes 610 may be placed or arrayed in accordance with any of numerous known paradigms. Electrodes 610 could be placed for use with dense array EEG or ambulatory EEG, or applications of equivalent placement for other modes of electrode placement (e.g., brain surface or deep brain).

Electrodes 610 provide the brain wave or voltage fluctuations they detect to a processor 620. Not shown, but optionally included, is a filter for filtering measurements received and conveyed by electrodes 610. A filter may be part of a processor 620 or a separate component. In either case, whether part of a processor or a separate component, a filter is connected to a processor 620 within the meaning of the description of the present invention herein. A processor 620 is a computer system programmed for the receipt, storage, modification, and application of information related to brain waves or other indicia of neural excitability received from electrodes 610. Processor 620 may be self-standing, such as a laptop or desktop computer, or may be portable such as to be worn by a subject, or may be implantable. A processor may contain a recording medium 630 which electronically stores data related to neural activity such as wave traces. As with a filter, a recording medium may be incorporated within or separate from and attached, or connected wirelessly or otherwise, to a processor 620, but in either case would be included with the processor for the purposes of the description of the invention provided herein. A processor may contain an extractor 640 which extracts instantaneous voltage amplitudes of biased oscillatory activity from the information provided by electrodes 610. An extractor 640 may be incorporated within or separate from and attached to a processor 620, but in either case would be included with the processor for the purposes of the description of the invention provided herein. Connected to the processor, wirelessly or otherwise, may be a neural stimulator 650. A neural stimulator 650 may be placed where measurement of neural excitability is desired for a given application, such as on the surface of the scalp in the case of EEG, the surface of the cortex in the case of ECoG, below the surface of and within the brain, on the surface of or within the spinal cord, etc. In some examples, an electrode and a neural stimulator may be incorporated into a single probe applied to a subject.

Not shown in FIG. 6, but optionally included, is an aggregator, either as part of processor 620 or connected to it, in either case being considered part of processor 620. An aggregator combines input from multiple recording electrodes, when present, to provide one output, or fewer outputs than there are inputs from recording electrodes, to a given neural stimulator. For example, information pertaining to neural excitability from more than one region may desirably be samples and used to correctly time the application of neural stimulation to one of those regions, or yet a different region.

Processor 620 directs neural stimulator 650 when to provide stimulation. Processor 620 may base the onset of stimulation to correspond to times of elevated neural activity as indicated from instantaneous voltage amplitudes of biased oscillatory activity extracted by the extractor. Timing of when to apply stimulation as a function of instantaneous voltage amplitudes of biased oscillatory activity may be calibrated based on test measurements. For example, calibration could be done experimentally by stimulating the brain during different values of instantaneous voltage, measuring the responses, and determining from the magnitude of the responses at given voltages the maximum threshold value that still produces a large fraction of the responses. An approximation that may not require additional calibration is to put the threshold value half-way between the minimum and maximum values of instantaneous voltage.

In another embodiment of the present invention, measurement of neural excitability may be conveyed to a subject whose neural excitability is being measured such that the subject may use the feedback received to further modify neural excitability, referred to as neurofeedback. Learning to control brain function has a number of different important applications. These include neurofeedback in which people learn to control measurements of oscillatory activity to improve symptoms of ADHD (Arns et al., 2015, Frontiers in Human Neuroscience, 9), chronic pain (Jacobs et al., 2015, NeuroRegulation, 2:86), and improve function in people with chronic stroke (Morone et al., 2015, Archives of Physical Medicine and Rehabilitation, 96:S7178). Such voluntary changes in oscillatory activity can also be used by a person to communicate their desires (Wolpaw et al., 2002, Clinical neurophysiology, 113:767-791). In accordance with the present invention, instantaneous amplitude of biased oscillations are used to define the neural excitability, or other brain state(s), feedback to subjects, providing a measurement of neural excitability that is more accurate than conventional measurements and therefor improving the effectiveness of the neurofeedback. That is, because instantaneous amplitude is a better descriptor of a current state of brain function (e.g., cortical excitability) compared to conventional measurements such oscillatory power, the performance of a neurofeedback system using the instantaneous amplitude in accordance with the present invention is an improvement over conventional technology.

Figure 7:
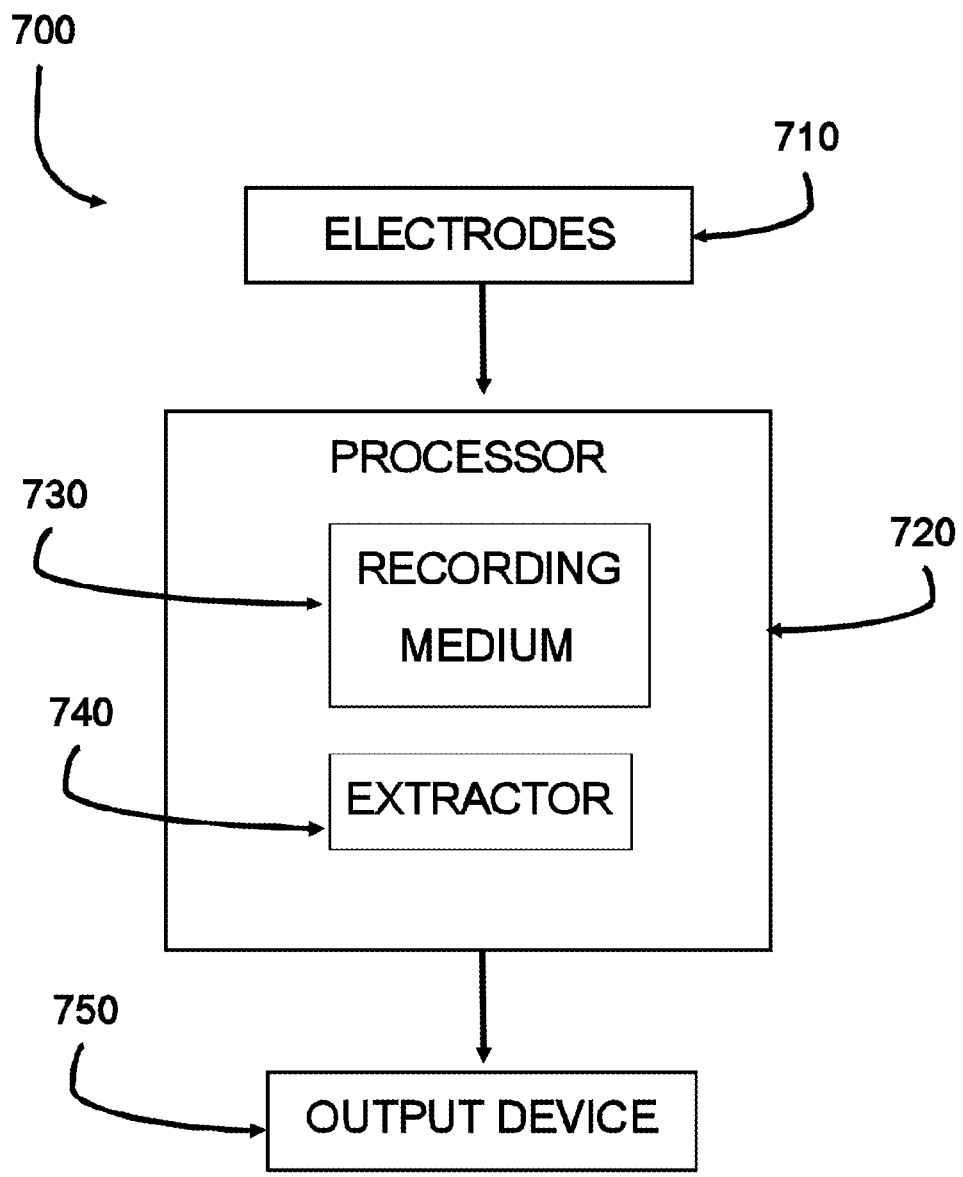
FIG. 7: A system for providing neural feedback in accordance with an embodiment of the present invention.

One non-limiting example of an embodiment of a neurofeedback system in accordance with the present invention is illustrated in FIG. 7. In many respects, such a system resembles a responsive neural stimulator such as depicted in FIG. 6. A principal difference is that, whereas a responsive neural stimulator has a neural stimulator 650 for applying neural stimulation to a subject, a neurofeedback system 700 in FIG. 7 has an output device 750. An output device may present salient stimuli to a subject whose neural excitability is being monitored so that the subject may be made aware of such level of excitability, or the absence thereof. By attempting to modify neural excitability, and receiving feedback from the output device, the subject may determine whether a desired effect on neural excitability is being obtained or, if not, accordingly modify the attempts to do so.

Referring to the non-limiting example shown in FIG. 7, shown is an embodiment of the present invention in the form of a neurofeedback system 700. Electrodes 710 are attached to a subject, such as a human subject, and can be placed where measurement of neural excitability is desired for a given application, such as on the surface of the scalp in the case of EEG, the surface of the cortex in the case of ECoG, below the surface of and within the brain, on the surface of or within the spinal cord, etc. Rather than multiple electrodes 710, simply one recording electrode may be placed on or within a subject, such as if there is only one locus from which information as to excitability state is desired. In addition to recording electrodes 710, reference electrodes may also be applied, in accordance with conventional population-level sampling techniques, as would be appreciated by those with ordinary skill in this field. Electrodes 710 may be placed or arrayed in accordance with any of numerous known paradigms. Electrodes 710 could be placed for use with dense array EEG or ambulatory EEG, or applications of equivalent placement for other modes of electrode placement (e.g., brain surface or deep brain).

Electrodes 710 provide the brain wave or voltage fluctuations they detect to a processor 720. Not shown, but optionally included, is a filter for filtering measurements received and conveyed by electrodes 710. A filter may be part of a processor 720 or a separate component. In either case, whether part of a processor or a separate component, a filter is connected to a processor 720 in accordance with the description of the present invention herein. A processor 720 is a computer system programmed for the receipt, storage, modification, and application of information related to brain waves or other indicia of neural excitability received from electrodes 710. Processor 720 may be self-standing, such as a laptop or desktop computer, or may be portable such as to be worn by a subject, or may be implantable. A processor may contain a recording medium 730 which electronically stores data related to neural activity such as wave traces. As with a filter, a recording medium may be incorporated within or separate from and attached, or connected wirelessly or otherwise, to a processor 720, but in either case would be included with the processor for the purposes of the description of the invention provided herein. A processor may contain an extractor 740 which extracts instantaneous voltage amplitudes of biased oscillatory activity from the information provided by electrodes 710. An extractor 740 may be incorporated within or separate from and attached to a processor 720, but in either case would be included with the processor 720 for the purposes of the description of the invention provided herein.

Connected to the processor 720, wirelessly or otherwise, may be an output device 750. An output device 750 may be any device configured to communicate changes in, increases in, decreases in, or maintenance of instantaneous voltage amplitudes, or any combination of two or more of the foregoing, to a participant in a neurofeedback session. Nonlimiting examples of an output device 750 include, in accordance with the present invention, a computer monitor, a light-emitting device, a speaker, an auditory device, an electrode, a vibrational feedback device, or a thermal feedback device. Any device that can convey, in a salient form, information extracted from measures of neural excitability may be used. For example, processor 720 may control graphics or text on a computer monitor, pitches or volumes of sound or sound recordings, patterns or colors or flashes of light, locations or patterns or speeds or strength of vibrational or other tactile feedback, or qualities of thermal or tactile electrical feedback.

Another example of an output device 750 is a prosthetic. Individuals with lost limbs, spinal cord injury, or neurological debilitations may be fitted with prosthetic limbs or structures to aid in movement of limbs. Conventionally, measurements of cortical activity are used to direct electromechanical aspects of such prosthetic devices to move, providing a level of a subject's control over the action of the prosthetic so as to restore some degree of neural control over behavior. However, these conventional methods, systems, and apparatuses, as with other conventional applications of measurements of neural excitability, suffer from poor precision, accuracy, specificity, and reliability of determining neural excitability. In accordance with the present invention, an output device 750 of a neurofeedback system, or comparable system, may include a prosthetic, such that a subject may determine from the motion or lack thereof of a prosthetic whether a brain state has been achieved and, if not, to modify neural activity so as to attain a state advantageous to desirable movement of the prosthetic. In like manner, measurements of instantaneous amplitude of biased oscillations may be used to propel vehicles such as mechanized wheelchairs, drive computerized speech production technology for subjects unable to speak, activate computer text production for written communication, activate a graphical user interface on a computer, etc., in accordance with the present invention. For many of these applications, it is not necessary that the subject is debilitated or suffering from any disorder or loss of function in order for the present invention to be used.

Not shown in FIG. 7, but optionally included, is an aggregator, either as part of processor 720 or connected to it, in either case being considered part of processor 720. An aggregator combines input from multiple recording electrodes, when present, to provide one output, or fewer outputs than there are inputs from recording electrodes, to a given output device 750. For example, information pertaining to neural excitability from more than one region may desirably be sampled and used to correctly time the display of salient feedback to a subject.

Processor 720 directs output device 750 when to provide salient feedback and in what manner. Processor 720 may base the onset and quality of feedback to correspond to times of elevated neural activity as indicated from instantaneous voltage amplitudes of biased oscillatory activity extracted by the extractor. It should be realized that, in accordance with the present invention, a single system can incorporate both a responsive neural stimulator and a neurofeedback system. Just as a responsive neural stimulator may have multiple neural stimulators 650, or a neurofeedback system may have more than one output device 750, a combined system may combine one or more neural stimulators and one or more output devices. For example, neurofeedback could be incorporated to assist a subject in influencing when or whether neural stimulation is applied.

EXAMPLES

The following examples are intended to illustrate particular embodiments of the present invention, but in no way limit the scope of the present invention.

As demonstrated in the following examples, instantaneous voltage of biased oscillations is a better measurement of cortical excitability than oscillatory power or oscillatory phase. ECoG signals from 28 human patients with epilepsy who had 58-134 ECoG electrodes implanted for the purpose of presurgical planning. Recording was accomplished at the bedside using the general-purpose BCI2000 software, which interfaced with eight 16-channel g.USBamp biosignal acquisition devices or a single 256-channel g.HIamp biosignal acquisition device. A splitter box routed signals simultaneously to the clinical monitoring system and to the BCI2000/amplifier system, and thereby supported continuous clinical monitoring. The signals were amplified, digitized at 1200 Hz, and stored by BCI2000. Electrode contacts distant from epileptic foci and areas of interest were used for reference and ground.

Each subject performed alternating sequences of repetitive movements of the hand (manipulating a Rubik's cube) or orofacial muscles (protruding and retracting the tongue or lips), passive listening (short stories presented with computer speakers), and periods of rest. In each trial, the subject was visually cued to the task by the words "solve Rubik's cube," "stick out tongue," "kiss," "listen carefully," or "stop and relax." Each task was performed for 15 seconds (except for passive listening, which was 17-36) seconds depending on which narrative was presented). The motor tasks were performed at a self-paced rate of about two repetitions per second. Each task was followed by a resting period of 15 seconds before the next task proceeded. One run consisted of 5 repetitions of this sequence over the course of 10.22 minutes (4.75 minutes rest, 1.25 minutes hand moving, 1.25 minutes tongue moving, 1.25 minutes lips moving, and 1.72 minutes passive listening). One initial run was typically recorded to familiarize the subject with the task. This initial run was not included in data analyses.

Before proceeding with analysis, the ECoG recordings were visually inspected offline and channels that did not contain clear ECoG signals (e.g., ground/reference channels, channels with broken connections, presence of environmental artifacts, or interictal activity) were removed from analysis. In addition, channels with excessive line noise were excluded prior to post-hoc analyses. To do this, we implemented an IIR peak filter (MATLAB™ iirpeak function), and excluded from further analyses those channels whose amplitude at 60 Hz was greater than or less than ten median average deviations from the median amount of that amplitude in all channels. The remaining locations were submitted to further analysis.

ECoG broadband gamma is widely recognized as a key measurement of cortical excitation, has been shown to directly drive the BOLD signal identified using fMRI, and has been shown to reflect the average firing rate of neurons directly underneath the electrode. Thus, ECoG broadband activity was used as an index of cortical excitation.

To extract oscillatory and broadband gamma activity, the ECoG signals were first high-pass filtered at 0.01 Hz and re-referenced to a common average reference (CAR). The CAR-filtered signal $s'_h$ at channel h using the following equation (1):

$$s'_h = s_h - \frac{1}{H}\sum_{q=1}^{H} s_q$$

$s_h$ was the original signal sample at a particular time, and H was all channels included in the CAR. The amplitude of oscillatory activity in the alpha band (8-12 Hz) was then extracted using a 6th order Butterworth band-pass filter implemented with zero phase lag (MATLAB™ filtfilt function), and derived broadband activity by applying a band-pass filter of 70-170 Hz. The amplitude envelope (i.e., square root of power) and phase estimates were then acquired for alpha/gamma activity by applying the Hilbert transform to the respective band-pass filtered time series.

For extraction of the model-based instantaneous amplitude, the instantaneous amplitude of biased oscillatory activity was extracted by first high-pass filtering the ECoG signals at 0.01 Hz and re-referencing to a common average reference (CAR). The CAR-filtered signal was then obtained, as described in Liu et al. (2015, Journal of Neural Engineering, 12:056008). The amplitude of oscillatory activity (S) in the alpha band (8-12 Hz) was then extracted using a 6th order Butterworth band-pass filter implemented with zero phase lag (MATLAB filtfilt function). The amplitude envelope (i.e., square root of power) for alpha activity (AA) was then obtained by applying the Hilbert transform to the band-pass filtered time series. The maximum amplitude bias was then calculated as $bias_{max}=(AA_{95}-AA_5)/2$ where $AA_{95}$ and $AA_5$ give the 95th and 5th percentile of all alpha activity values AA. At each point in time, bias was then subtracted for the specific value of AA at that time from the signal S at that time: $S'=S-(AA_{95}-AA)/(AA_{95}-AA_5)*bias_{max}$. S' gave the instantaneous amplitude of the biased oscillation.

Evaluating the relationship between specific measurements of cortical excitability and cortical excitability required that a particular cortical location does vary in its excitation throughout the dataset. To ensure that this is the case, in each subject, only those locations were selected for subsequent analyses where broadband gamma activity changed substantially between rest and one of the two tasks (movement of the hand (i.e., motor task) and passive listening (i.e., auditory task)). To do this, first, separately for each task and location, the pairwise Pearson's coefficient of determination ($r^2$) between task labels (i.e., task and rest) and broadband gamma power was calculated. From all channels those with $r^2$ values larger than 0.2 were selected. This yielded 82 channels for the motor task and, separately, 44 channels for the auditory task.

Figure 8:
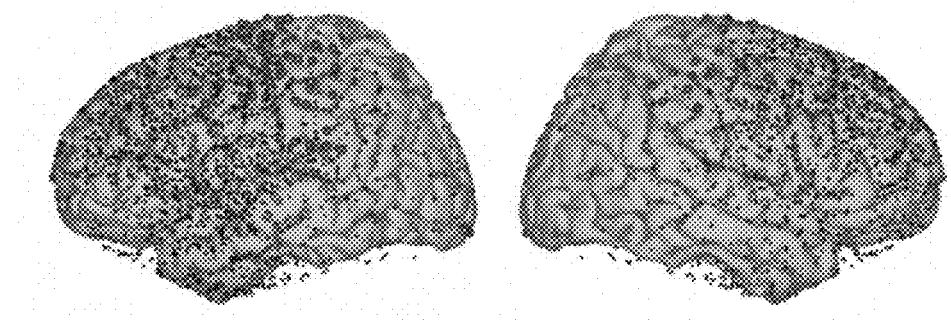
FIG. 8: Electrode placements from all 28 subjects.

FIG. 8 shows electrode locations from each neural hemisphere of all 28 subjects. Electrodes are projected onto the common MNI template for ease of visualization. Open circles indicate locations whose activity was significantly modulated by the motor task or auditory task. Black dots show electrode locations not related to either of the behavioral tasks.

A model was established that related each of the three oscillatory measurements (power, phase, and instantaneous amplitude) to broadband gamma, determined the fit of the model at each location, and evaluated, based on the distribution of model fits across all locations which of the three models was the best fit for the data. There are different ways to implement the elements of this procedure in accordance with the present invention. The principal results described here have been produced using the configuration described below.

For each location, a model was established that described the relationship between alpha power, phase, or amplitude with broadband gamma activity. Based on preliminary testing, a sigmoid function was used to model the relationship between alpha power/alpha amplitude and broadband gamma. Based on previous literature, publicly available and known to those of ordinary skill in the field, a cosine function was used to model the relationship between alpha phase and broadband gamma. Broadband power decreases for larger alpha power. Broadband power is largest during the through of an oscillation.

MATLAB™ was used to derive the sigmoid fits. The sigmoid fits used the 5th-95th percentiles of the data, whereas the sinusoid fit used all data (as they are confined to and evenly distributed from $0\pi-2\pi$).

To test how well alpha power, phase, and instantaneous voltage predicted cortical excitability (as indexed by broadband gamma), a-priori models were chosen to fit data from task-modulated channels in each of the three cases. Since at high alpha power/voltage, broadband gamma activity should be low, and at low alpha power/voltage, broadband gamma amplitudes should be high, a sigmoid model is a reasonable choice to fit to the power and instantaneous voltage cases. For the phase case, a sinusoid (fixed to one period of the waveform with variable amplitude and phase offset) was fit. Goodness-of-fits were determined by Pearson's coefficient of determination (in this case, equivalent to a least-squares fit to the model from residuals) between the model and the data. To determine model fits, broadband gamma values were binned into linearly spaced bins based on alpha power, phase, or instantaneous voltage, depending on case. To avoid statistical biases created when the number of data points varies across bins, a bootstrap statistic was applied. To do this, the bin with the smallest number of data points across all three cases within a channel was identified. This number was then used to subsample data across all bins such that each bin represented a mean value derived from the same number of data points, and finally calculated the model fit ($r^2$) in each case. This procedure was re-run 1000 times using sample-with-replacement to subsample data in each of the 1000 permutations, and the average $r^2$ from the resulting 1000 $r^2$ values for each case in each channel calculated.

To determine which measurement (power, phase, or amplitude) best predicted cortical excitability (as indexed by broadband gamma activity), distributions of alpha phase fits were compared to instantaneous alpha voltage fits, alpha phase fits to alpha power (amplitude envelope) fits, and instantaneous alpha voltage fits to alpha power (amplitude envelope) fits. Both a parametric paired t-test and also a nonparametric paired equivalent were used. For t-tests, a Fisher's z-transform was applied to make all distributions of $r^2$ values Gaussian before applying the paired t-test. A nonparametric paired Wilcoxon's Signed Rank test was also run on the original (non-Fisher transformed) distributions. Finally, the same tests were applied to $r^2$ values derived from all data (i.e., not binned).

Figure 9A:
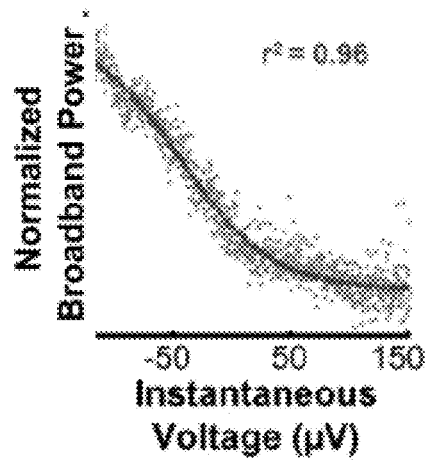
FIG. 9A: A graphical comparison between instantaneous oscillatory amplitude (x-axis) and cortical excitability (y-axis).
Figure 9B:
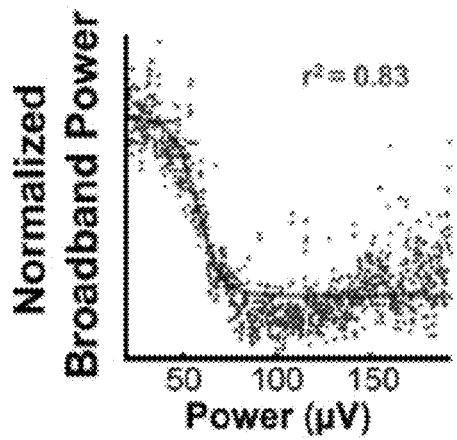
FIG. 9B: A graphical comparison between oscillatory power (x-axis) and cortical excitability (y-axis).
Figure 9C:
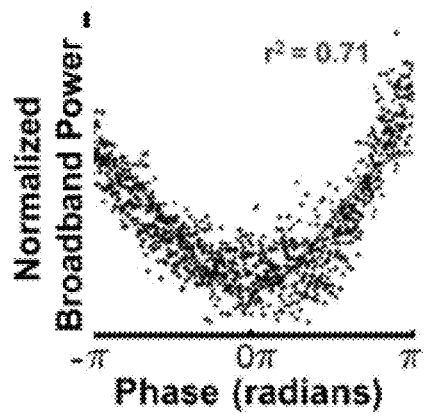
FIG. 9C: A graphical comparison between oscillatory phase (x-axis) and cortical excitability (y-axis).
Figure 10:
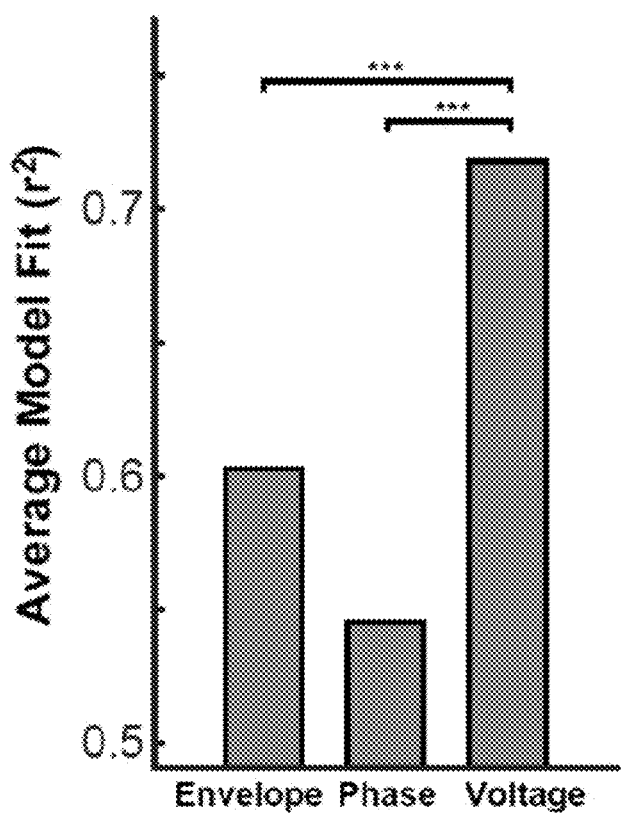
FIG. 10: Average model fits for power, phase, and instantaneous oscillatory voltage.

The large ECoG-based dataset comprised of 28 subjects who had a total of 2,442 electrodes implanted (58-134 per subject). Each subject alternated between rest and different tasks that included manipulation of a Rubik's cube (motor task) and listening to a spoken story (auditory task). These two different tasks produced task-related changes in broadband gamma activity in a total of 126 locations (82 for motor task and 44 for auditory task). For each of these locations, the principal measurement of underlying oscillatory activity in the alpha band (power, phase or instantaneous voltage) was related to broadband gamma activity by fitting a sigmoid function (for power or instantaneous voltage) or a cosine function (for phase) to the data. FIGS. 9A-9C show the underlying data (dots) and model fits (lines) for each of the three measurements for an exemplary location. In this location, the model fit, as assessed by the $r^2$ derived from least-squares regression, was higher for instantaneous voltage (0.96) as shown in FIG. 9A than for oscillatory power or phase (0.83 and 0.71, respectively), as shown in FIGS. 9B and 9C, respectively. Critically, the instantaneous voltage was a better predictor of cortical excitability (as assessed by broadband gamma activity) not only at this individual exemplary location, but also across all locations across all 28 subjects, as shown in FIG. 10.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A responsive neural stimulator comprising:
   one or more recording electrodes connected to a filter;
   a processor connected to the filter wherein the processor comprises a recording medium for recording brain waves detected by the one or more recording electrodes and an extractor for extracting instantaneous voltage amplitudes of biased oscillatory activity, and wherein the biased oscillatory activity comprises asymmetrically distributed peak/trough amplitudes; and
   a neural stimulator connected to the processor, wherein the processor, the neural stimulator, or both are configured to apply neural stimulation via the neural stimulator when a predetermined state of neuronal excitability is detected, wherein a state of relatively higher neuronal excitability comprises a relatively lower instantaneous voltage amplitude extracted by the extractor.

2. The responsive neural stimulator of claim 1, wherein the one or more recording electrodes comprise scalp electroencephalography electrodes, brain-surface electrocorticography electrodes, within-brain-local field potential electrodes, or any combination of two or more of the foregoing.

3. The responsive neural stimulator in claim 1, wherein the neural stimulator is a brain-surface stimulator or a within-brain implantation stimulator.

4. The responsive neural stimulator of claim 2, wherein the one or more recording electrodes comprise scalp electroencephalography electrodes and the scalp electroencephalography electrodes comprise dense array electrodes or ambulatory electrodes.

5. The responsive neural stimulator of claim 1, wherein the one or more recording electrodes, the neural stimulator, the processor, or any combination of two or more of the foregoing, are indwelling or portable.

6. The responsive neural stimulator of claim 3, wherein the one or more recording electrodes comprise indwelling brain-surface electrocorticography electrodes and the processor is portable or indwelling.

7. A method of using the responsive neural stimulator of claim 1, wherein using comprises applying stimulation via the neural stimulator when said predetermined state of neuronal excitability is detected.

8. A system for providing neurofeedback comprising:
one or more recording electrodes connected to a filter;
a processor connected to the filter wherein the processor comprises a recording medium for recording brain waves detected by the one or more recording electrodes and an extractor configured to extract instantaneous voltage amplitudes of biased oscillatory activity comprising asymmetrically distributed peak/trough amplitudes; and
an output device connected to the processor and configured to communicate changes in, increases in, decreases in, or maintenance of instantaneous voltage amplitudes, or any combination of two or more of the foregoing, to a participant in a neurofeedback session.

9. A system of claim 8, comprising a plurality of output devices connected to the processor and configured to communicate changes in, increases in, decreases in, or maintenance of instantaneous voltage amplitudes, or any combination of two or more of the foregoing.

10. The system of claim 8, wherein the one or more recording electrodes comprise scalp electroencephalography electrodes, brain-surface electrocorticography electrodes, within-brain local field potential electrodes, or any combination of two or more of the foregoing.

11. The system of claim 10, wherein the one or more recording electrodes comprise scalp electroencephalography electrodes and the scalp electroencephalography electrodes comprise dense array electrodes or ambulatory electrodes.

12. The system of claim 8, wherein the output device comprises a display device, a computer monitor, a light-emitting device, a speaker, an auditory device, an electrode, a vibrational feedback device, or a thermal feedback device.

13. The system of claim 12, wherein the output device comprises a light-emitting device configured to communicate changes in, increases in, decreases in, or maintenance of instantaneous voltage amplitudes, or any combination of two or more of the foregoing by displaying visual stimuli.

14. The system of claim 12, wherein the output device comprises a speaker configured to communicate changes in, increases in, decreases in, or maintenance of instantaneous voltage amplitudes, or any combination of two or more of the foregoing by producing auditory stimuli of a pitch, volume, or duration, or any combination of two or more of the foregoing.

15. The system of claim 8, further comprising an aggregator configured to aggregate instantaneous voltage amplitudes detected by two or more electrodes and wherein the output device is configured to communicate changes in, increases in, decreases in, or maintenance of, or any combination of two or more of the foregoing, aggregated instantaneous voltage amplitudes.

16. The system of claim 15, wherein the one or more recording electrodes comprise scalp electroencephalography electrodes, brain-surface electrocorticography electrodes, within-brain local field potential electrodes, or any combination of two or more of the foregoing.

17. The system of claim 16, wherein the one or more recording electrodes comprise brain-surface electrocorticography electrodes and the brain-surface electrocorticography electrodes comprise dense array electrodes or ambulatory electrodes.

18. The system of claim 15, wherein the output device comprises a display device, a computer monitor, a light-emitting device, a speaker, an auditory device, an electrode, a vibrational feedback device, or a thermal feedback device.

19. The system of claim 18, wherein the output device comprises a light-emitting device configured to communicate changes in, increases in, decreases in, or maintenance of aggregated instantaneous voltage amplitudes, or any combination of two or more of the foregoing by displaying visual stimuli.

20. The system of claim 18, wherein the output device comprises a speaker configured to communicate changes in, increases in, decreases in, or maintenance of aggregated instantaneous voltage amplitudes, or any combination of two or more of the foregoing, by producing auditory stimuli of a pitch, volume, or duration, or any combination of two or more of the foregoing.

* * * * *